(12) United States Patent
Boese

(10) Patent No.: US 7,428,291 B2
(45) Date of Patent: Sep. 23, 2008

(54) OPERATING METHOD FOR AN X-RAY APPARATUS, OPERATING METHOD FOR A COMPUTER, AND ITEMS CORRESPONDING TO SAID OPERATING METHODS

(75) Inventor: Jan Boese, Eckental (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/518,569

(22) Filed: Sep. 8, 2006

(65) Prior Publication Data
US 2007/0053481 A1  Mar. 8, 2007

(30) Foreign Application Priority Data
Sep. 8, 2005   (DE) ................. 10 2005 042 798

(51) Int. Cl.
*G01N 23/00* (2006.01)
(52) U.S. Cl. ............................. 378/8; 378/16
(58) Field of Classification Search ................ 378/8, 378/4, 15, 16, 20
See application file for complete search history.

(56) References Cited

U.S. PATENT DOCUMENTS

| | | | | |
|---|---|---|---|---|
| 5,377,252 | A * | 12/1994 | Liebetruth | 378/151 |
| 6,504,893 | B1 * | 1/2003 | Flohr et al. | 378/8 |
| 6,909,769 | B2 | 6/2005 | Bruder et al. | |
| 7,305,062 | B2 | 12/2007 | Hambüchen et al. | |
| 2002/0181645 | A1 * | 12/2002 | Bruder et al. | 378/8 |
| 2004/0023133 | A1 | 2/2004 | Shimbori et al. | |
| 2007/0030945 | A1 | 2/2007 | Boese et al. | |

FOREIGN PATENT DOCUMENTS

| | | |
|---|---|---|
| DE | 4303748 C2 | 8/1994 |
| DE | 10313510 A1 | 10/2004 |
| DE | 10 2004 061 933 A1 | 7/2006 |
| DE | 10 2005 016 472 | 10/2006 |

* cited by examiner

*Primary Examiner*—Hoon Song

(57) ABSTRACT

An X-ray apparatus has a recording assembly and a control device. The recording assembly has an X-ray source and detector, an aperture device, and a swiveling axis. An object having an object area constant and an object area changing over time is arranged that the object area changing over time is located in the vicinity of a crossover area of the swiveling axis and the connecting line from the X-ray source and the detector. The detector registers projections of the object and conveys projections to the control device. The aperture device is open wider during swiveling operations. A computer accepts the projections and determines a basic projection whose status information tallies with nominal status information and an additional projection having a wider opening of the aperture device than all other projections registered at the respective angular position. The computer determines a reconstruction projection based on the basic and additional projections.

21 Claims, 8 Drawing Sheets

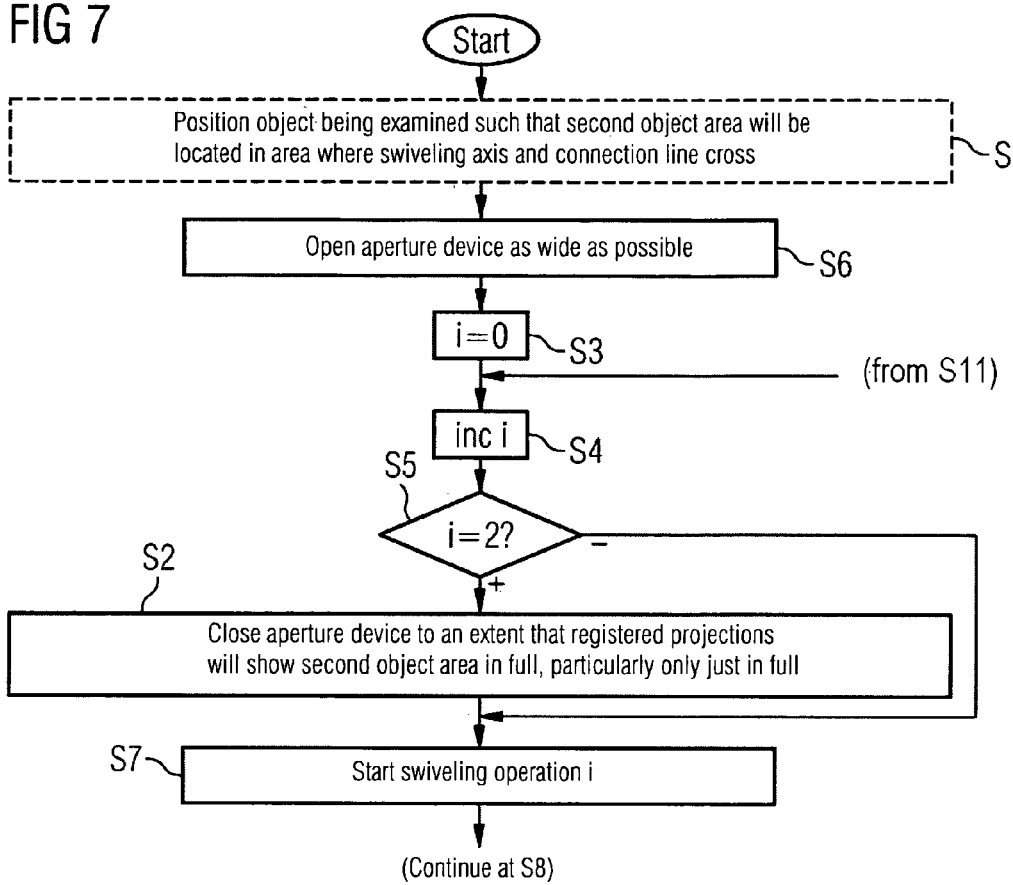
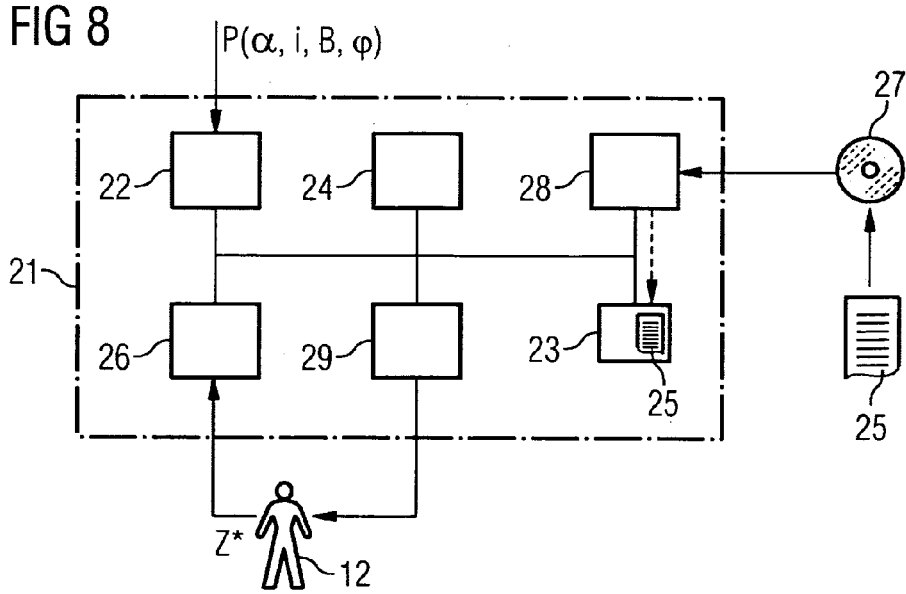

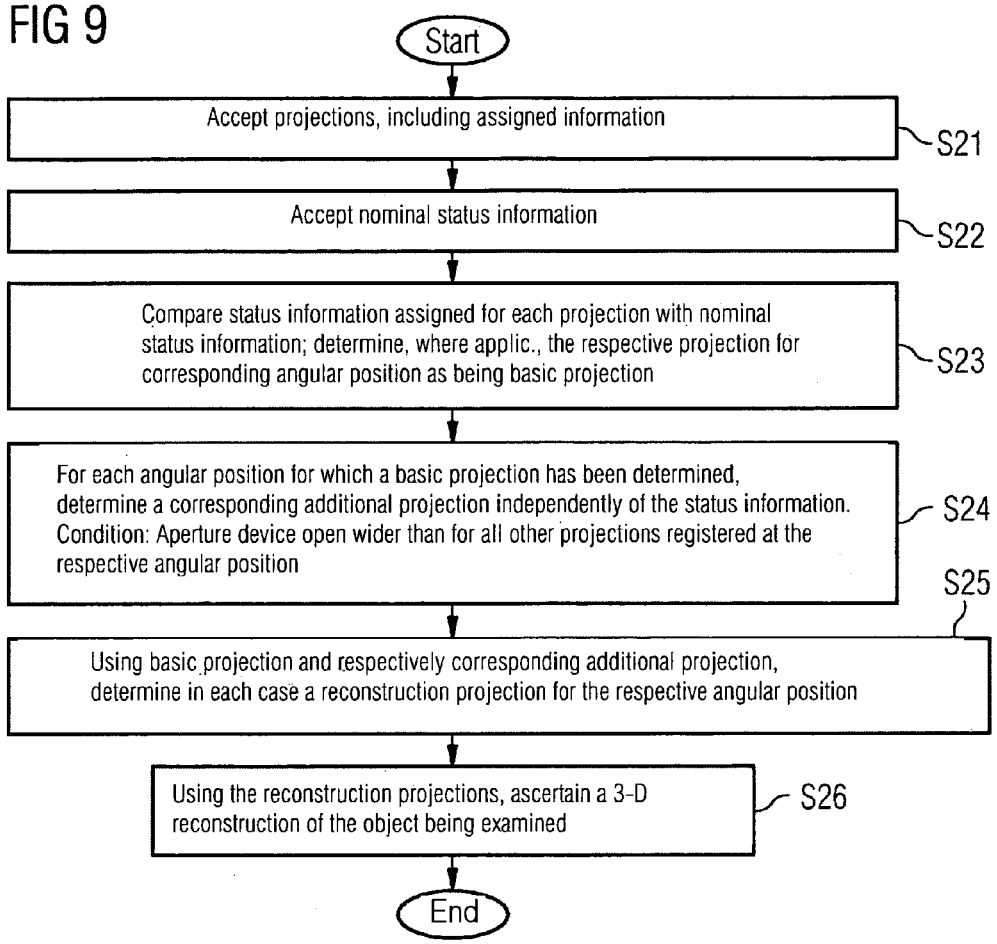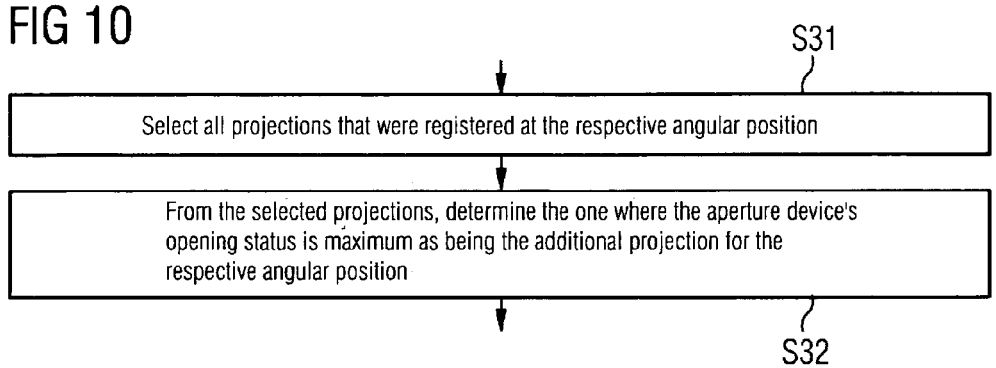

OPERATING METHOD FOR AN X-RAY APPARATUS, OPERATING METHOD FOR A COMPUTER, AND ITEMS CORRESPONDING TO SAID OPERATING METHODS

CROSS REFERENCE TO RELATED APPLICATIONS

This application claims priority of German application No. 10 2005 042 798.7 filed Sep. 08, 2005, which is incorporated by reference herein in its entirety.

FIELD OF THE INVENTION

The present invention relates to an operating method for an X-ray apparatus and an X-ray apparatus used in a medical procedure. The present invention also relates to an operating method for a computer for a subsequent three-dimensional reconstruction of projections recorded by the X-ray apparatus.

BACKGROUND OF THE INVENTION

Operating methods, data carriers, control devices, and X-ray apparatuses of said kind are generally known. They are used in particular for recording two-dimensional projections for a subsequent three-dimensional reconstruction of objects being examined.

The following procedure is broadly customary for recording the two-dimensional projections of the object being examined:

The object being examined or, as the case may be, the relevant area thereof is arranged in such a way that the relevant object area is locked in the crossover area of the swiveling axis and connecting line or, as the case may be, in the vicinity thereof. If, say, the object being examined is a person, then that person's heart or brain could be the relevant object area. In that case, for instance, a patient trolley on which the examinee is lying will be moved in such a way that the heart or, as the case may be, brain will be located in the above-cited crossover area.

A human heart, in particular, undergoes an iterative change—of course—because it has to beat, and so moves. It is, however, also possible for the relevant object area to change over time, independently of any movement. Consider, for example, how a contrast medium spreads in a vascular system or in an organ being supplied with blood (a muscle, including a heart muscle, the brain, the liver, . . . ). Particular consideration is given within the scope of the present invention to such cases in which the relevant object area changes over time.

The object being examined having been placed in position, the control device will drive the recording assembly in such a way that it will be swiveled around the swiveling axis. During said swiveling operation the control device drives the recording assembly in such a way that the X-ray detector will register two-dimensional projections of the object being examined in a multiplicity of angular positions, then convey them to the control device. The control device stores the projections conveyed to it, the corresponding angular positions, and status information about the object area changing over time.

In the older German patent application 10 2005 016 472.2 dated Apr. 8, 2005, not published by the submission date of the application for the present invention, a variant of the above-described method is described wherein not just a single swiveling operation is performed but a plurality thereof. Said older, not previously published application is not, though, a generally known state of the art but is to be considered only within the scope of the German patent-issuing process and, in the course thereof, only within the scope of the examination for novelty.

The two-dimensional projections of the object being examined that were registered for an X-ray apparatus applying the above-mentioned operating methods serve as the basis for a subsequent three-dimensional reconstruction, by means of a computer, of the object being examined.

It is furthermore described in the already mentioned German patent application 10 2005 016 472.2 dated Apr. 8, 2005, how, for each angular position for which the computer has determined a basic projection, to check whether an additional projection can also be determined, and, where applicable, to determine said additional projection also. It is crucial during said check for the status information of the additional projection also to correspond to the nominal status information.

If the computer determines an additional projection, it will determine a reconstruction projection for the respective angular position using the respective basic projection and respective additional projection. If it is unable to determine an additional projection, then the basic projection of the respective angular position will correspond to the reconstruction projection. The computer in each case ascertains the three-dimensional reconstruction using the reconstruction projections.

To be on the safe side, attention is at this point again drawn to the fact that the German patent application 10 2005 016 472.2 is not a generally known state of the art but is to be considered only within the scope of the German patent-issuing process and, in the course thereof, only within the scope of the examination for novelty.

It is furthermore described in the older German patent application 10 2004 061 933.6 dated Dec. 22, 2004, likewise not published by the submission date of the application for the present invention, that the two-dimensional projections are registered by means of two recording assemblies, with the X-ray detectors of the recording assemblies being of different size. In this case, for each angular position for which it has determined a basic projection the computer also determines an additional projection. The additional projection is independent of the status information. It is determined through having been registered by means of the larger of the two X-ray detectors. The computer determines in each case a reconstruction projection for the respective angular position using the basic projection and respectively corresponding additional projection. Using the reconstruction projections, the computer then ascertains the three-dimensional reconstruction of the object being examined. It applies also to the patent application 10 2004 061 933.6 that it is not a generally known state of the art but is to be considered only within the scope of the German patent-issuing process and, in the course thereof, only within the scope of the examination for novelty.

Two-dimensional projections of an object being examined for subsequently determining a three-dimensional reconstruction of said object are registered according to the prior art by means of, for example, angiography systems or what are termed C-arc systems, in particular mobile C-arc systems. The recording assembly is for that purpose swiveled through a swivel-angle range, which is to say between two final angular positions, around a swiveling axis. The swivel-angle range is as a rule greater than 180°, for example 200 to 225°. The three-dimensional reconstruction is determined according to, for instance, the Feldkamp algorithm generally known to persons skilled in the relevant art.

For certain applications it is necessary to perform a plurality of swiveling operations and to register two-dimensional projections during each of said operations. An instance of an application of said type is time-resolved heart imaging as described in, for example, the older German patent application 10 2005 016 472.2 dated Apr. 8, 2005. Perfusion measuring is another possible application.

The object being examined must of course also be X-rayed a corresponding number of times when projections are registered a number of times. The object being examined will consequently have a relatively high X-ray exposure.

To reduce the X-ray exposure it is already known how only to apply the full X-ray dosage when the object area changing over time (for example a person's heart) is momentarily in a phase condition requiring to be reconstructed. This procedure can, though, only be applied when it is known a priori in which phase condition the object area changing over time is to be reconstructed. This method for reducing the dosage cannot be applied if said phase condition is not known or if reconstructing is to be performed for a plurality of phase conditions.

To determine three-dimensional reconstructions it is necessary to use as large as possible an area of the X-ray detector and mask as little image information as possible through collimating of the X-ray beam. Artifacts will otherwise occur as a result of cut-off projections. Artifacts of said type are familiar to persons skilled in the relevant art as what are termed "truncation artifacts". That is why all swiveling operations are performed in the prior art with a fully opened aperture device.

SUMMARY OF THE INVENTION

The present invention relates to an operating method for an X-ray apparatus having a recording assembly and a control device, with the recording assembly having an X-ray source, an aperture device, and an X-ray detector, with the X-ray source and X-ray detector being diametrically opposite one another with reference to a swiveling axis, and the aperture device being arranged between the X-ray source and the swiveling axis along a connecting line from the X-ray source to the X-ray detector.

The present invention relates further to a data carrier having a computer program, stored thereon, for a control device of an X-ray apparatus for implementing an operating method of said type. The present invention also relates to a control device for an X-ray apparatus, having a program storage in which is stored a computer program so that the control device will implement an operating method of said type when the computer program is invoked.

The present invention relates furthermore to an X-ray apparatus having a control device and a recording assembly,
- wherein the recording assembly has an X-ray source, an aperture device, and an X-ray detector,
- wherein the X-ray source and the X-ray detector are diametrically opposite one another with reference to a swiveling axis,
- wherein the aperture device is arranged between the X-ray source and the swiveling axis along a connecting line from the X-ray source to the X-ray detector,
- wherein the control device is embodied as last described and connected to the recording assembly to the effect that the X-ray apparatus can be operated according to an operating method of such type.

The present invention thus relates also to an operating method for a computer,
- wherein the computer accepts a number of two-dimensional reconstructions of an object being examined,
- wherein the object being examined had an object area constant over time and an object area changing over time and was arranged in such a way that the object area changing over time was located in the vicinity of a swiveling axis around which a recording assembly was swiveled between two final angular positions while the projections were being registered,
- wherein the recording assembly had an X-ray source and an X-ray detector,
- wherein the X-ray source and the X-ray detector were diametrically opposite one another with reference to a swiveling axis and the object area changing over time was located in the vicinity of a crossover area of the swiveling axis and connecting line,
- wherein the projections were registered by the X-ray detector in a multiplicity of angular positions,
- wherein each accepted projection has been assigned the corresponding angular position as well as status information about the object area changing over time,
- wherein for each of a number of angular positions the computer determines a basic projection whose status information corresponds to nominal status information,
- wherein, using the basic projections, the computer ascertains a three-dimensional reconstruction of the object being examined.

A first object of the present invention is to provide an operating method for an X-ray apparatus along with the corresponding devices by means of all of which the applied X-ray dosage can be reduced, with no appreciable detriment to the quality of the three-dimensional reconstruction, when a plurality of swiveling operations are performed. The purpose in particular is to avoid the above-mentioned truncation artifacts.

A second object, corresponding thereto, of the present invention is to provide an operating method for a computer along with the corresponding devices by means of all of which a three-dimensional reconstruction of the object being examined can be determined with high quality using the two-dimensional projections registered according to the operating methods and devices that achieve the first object. The purpose in particular is to avoid the above-mentioned truncation artifacts.

The objects are achieved by an operating method and an equipment according to the claims.

According to the invention, the X-ray apparatus is therefore operated within the scope of registering projections in such a way that the recording assembly performs a swiveling operation not just once but several times, with said assembly being swiveled around the swiveling axis during each swiveling operation, the angle ranges of the swiveling operations at least overlapping, and the X-ray detector registering two dimensional projections of the object being examined in each of a multiplicity of angular positions, and conveying said projections to the control device. What, though, is crucial is that the control device drives the recording assembly in such a way that the aperture device is open wider during one of the swiveling operations than during the other swiveling operations.

While the three-dimensional reconstruction of the object being examined is being determined, the computer is inventively operated in such a way that it will also determine an additional projection for each angular position for which it has determined a basic projection, with the respective additional projection being independent of the status information and being determined by the fact that the aperture device was in its specific case open wider than in the case of all other projections that were registered at the respective angular position. Using the basic projections and respectively corresponding additional projections, the computer then determines a reconstruction projection for each respective angular position and ascertains the three-dimensional reconstruction of the object being examined using the reconstruction projections.

The aperture device is preferably open as wide as possible during one swiveling operation. That is because truncation artifacts will then be avoided as far as system engineering will allow. By contrast, during the other swiveling operations the aperture device preferably remains open sufficiently wide for the projections registered during said operations to show the object area changing over time at least substantially in full. That is because all the relevant image information will then also be registered during the other swiveling operations.

The aperture device preferably remains open sufficiently wide during the other swiveling options for the projections registered during said operations to show the object area changing over time only just in full. That is because the X-ray exposure of the object being examined will then be minimized.

The one swiveling operation during which the aperture device is open wider than during the other swiveling operations can in principle be any of the swiveling operations. The one swiveling operation will as a rule, though, be either that which is first in time or that which is last in time. The swiveling operation that is last in time is particularly advantageous. That is because the aperture device can then be precisely adjusted for example before the first swiveling operation and only operated (=opened) before the last swiveling operation.

The control device preferably also stores the respective opening status of the aperture device. That is because it will then be easy, using said information, to subsequently determine the additional projections. It will otherwise be necessary during subsequent evaluation for the computer to ascertain the additional projections using the projections as such.

It is possible for the object area changing over time to perform an iterative change. A typical example of this is a beating human heart. In this case the status information is preferably information about a phase condition of the object area changing over time.

If the speed with which the object area changing over time changes is sufficiently slow, then it is alternatively also possible for the status information to be characteristic of the respective swiveling operation during which the respective projection is registered.

It is in individual cases possible for the basic projection of an angular position and the additional projection of an angular position to be identical to each other. In that case, of course, the reconstruction projection will correspond to the basic projection or, as the case may be, additional projection. The basic projection and the additional projection of a specific angular position are, though, as a rule mutually different projections. In that case the computer will ascertain the reconstruction projection by updating the additional projection in the area corresponding to the basic projection using the basic projection, and otherwise retain the additional projection unchanged.

In the simplest case the computer will replace the additional projection in the area corresponding to the basic projection with the basic projection only. It is, however, also possible for the area corresponding to the basic projection to have a core and an edge area surrounding the core and for the computer to replace the additional projection in the core with the basic projection and to take account in the edge area of both the basic projection and the additional projection. More compute bound though it is, this procedure will nonetheless result in a better quality three-dimensional reconstruction. For example it is possible for the computer to locally merge the additional projection and the basic projection into each other in the edge area.

If the basic projection contains elements that were caused by the object area that is constant over time, then it is possible for the computer to register the basic projection with regard to the corresponding additional projection using said elements of the basic projection. The quality of the three dimensional reconstruction will be improved even further thereby.

BRIEF DESCRIPTION OF THE DRAWINGS

Further advantages and details will emerge from the following description of an exemplary embodiment in conjunction with the drawings. Shown schematically in FIG. 1 is a block diagram of an X-ray apparatus,
FIG. 7 is a flowchart,
FIG. 8 is a block diagram of an evaluation computer,
FIGS. 9 to 12 are flowcharts.

DETAILED DESCRIPTION OF THE INVENTION

Figure 1:
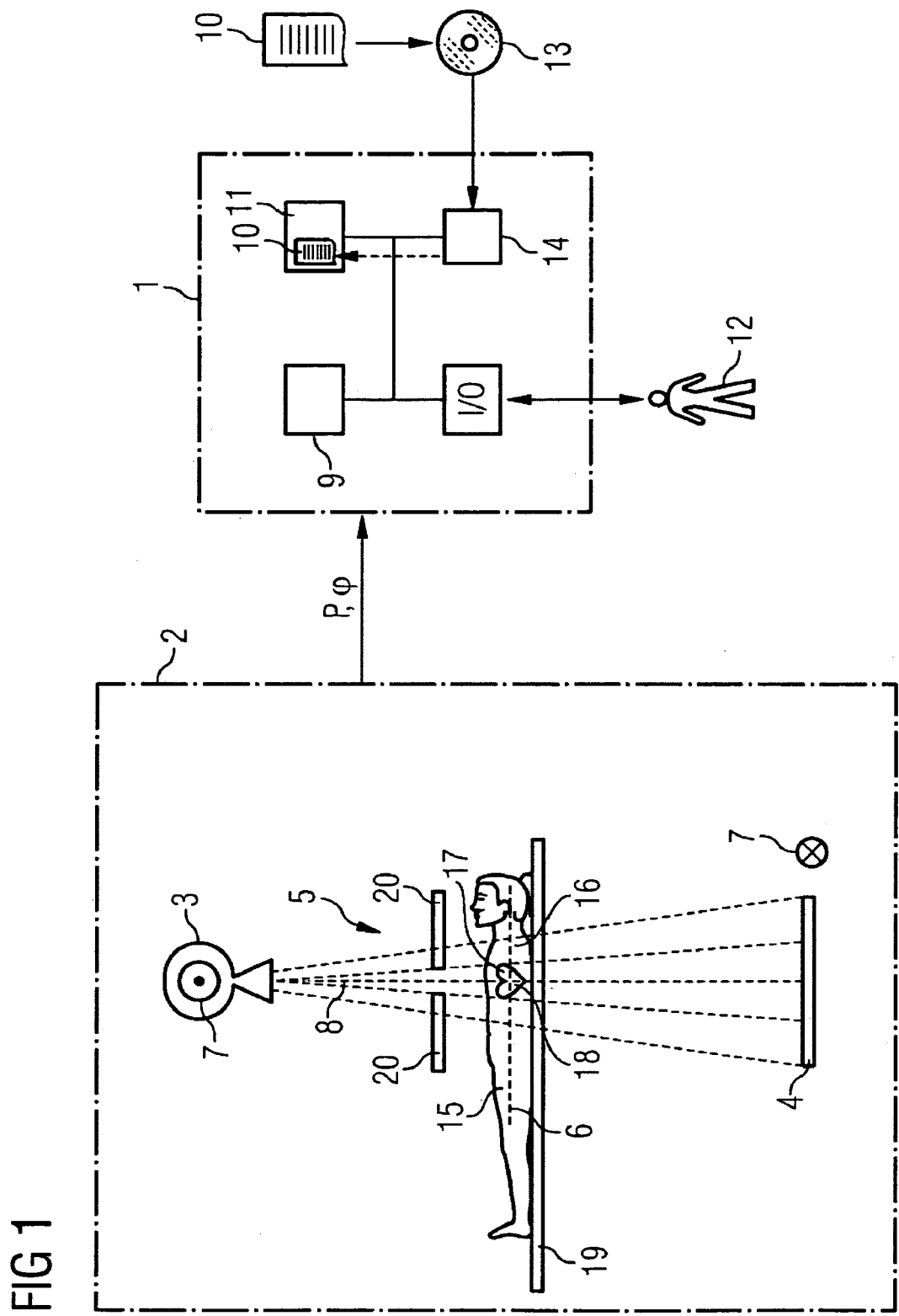

According to FIG. 1 an X-ray apparatus has a control device 1 and a recording assembly 2. The recording assembly 2 has an X-ray source 3, an X-ray detector 4, and an aperture device 5. The recording assembly 2 can be swiveled as a unit around a swiveling axis 6. That is indicated in FIG. 1 by relevant symbols 7. The circle with the point therein here corresponds to a movement out of the plane of projection; the circle with the cross therein here corresponds to a movement into the plane of projection.

The X-ray source 3 and the X-ray detector 4 are diametrically opposite one another with reference to a swiveling axis 6. The aperture device 5 is arranged between the X-ray source 3 and the swiveling axis 6 along a connecting line 8 from the X-ray source 3 to the X-ray detector 4.

The control device 1 is connected in terms of effect to the recording assembly 2 such that it is able to control the recording assembly 2. It is preferably embodied as a software-programmed control device 1. It therefore has a processor unit 9 which, when operating, executes a computer program 10 that determines the operating mode of the control device 1 and hence also of the X-ray apparatus overall. The computer program 10 is stored in a program storage 11 of the control device 1. It can be invoked by means of a corresponding call instruction by an operator 12 of the X-ray apparatus via an input/output interface I/O. When this is done, the computer program 10 will be executed and the X-ray apparatus operated in a manner that will be explained in more detail further down.

The computer program 10 must of course have been stored in the control device 1. For this purpose, a data carrier 13, on which the computer program 10 is stored, can, for example, be connected in data engineering terms to the control device 1 via a corresponding interface 14 of the control device 1. The control device 1 is in this case able to transfer the computer program 10 from the data carrier 13 and store it in the program storage 11.

Prior to implementing of the inventive operating method for the X-ray apparatus, the object being examined 15 is first placed into position in the recording assembly 2. The object being examined 15—frequently a person 15—has a first object area 16 and a second object area 17. The first object area 16 can within the scope of the present invention be regarded as being constant over time. The second object area 17 can within the scope of the present invention be regarded as changing over time.

If, say, the intention is to register recordings of the human heart, then this will as a rule be done over a period of time during which the person 15 has paused in breathing. During that period of time the skeletal area (arms, thorax, spinal column, . . . ), for example, of the person 15 can thus be regarded as being constant over time. By contrast, the heart of the person 15 and its surrounding area will move during said period of time because the heart of the person 15 is of course beating. The second object area 17 corresponds in this case to the human heart and its surrounding area, and the first object area 16 to the remainder of the person 15.

Within the subject matter just explained the change over time in the second object area 17 is a movement of the second object area 17. Changes in the second object area 17 are, though, also conceivable with no movements in the second object area 17. An example of a change over time of said type is the introduction and subsequent flushing out of a contrast medium into/from a vascular system or, as the case may be, its surrounding area, for example as part of a perfusion-determining procedure.

Regardless of the type of change over time involved, the object being examined 15 is placed into position in such a way that the second object area 17 changing over time will be located in the vicinity of a crossover area 18 in which the swiveling axis 6 and the connecting line 8 cross over. The swiveling axis 6 and the connecting line 8 preferably even cross over within the second object area 17. For example a patient trolley 19 can be moved accordingly either manually or, with the control device 1 being activated intermediately, mechanically. Registering of the two-dimensional projections P of the object being examined 15 takes place once the object being examined 15 has been placed into position. This is done according to FIG. 2 as follows:

As mentioned already, the object being examined 15 is first placed into position in a step S1 in such a way that the second object area 17 will be located in the crossover area 18 of the swiveling axis 6 with the connecting line 8 or, as the case may be, at least in the vicinity thereof. Step S1 is not, though, a mandatory component of the operating method implemented by the control device 1. It could also be performed manually. It is thus only drawn as a dashed line in FIG. 2.

Figure 3:
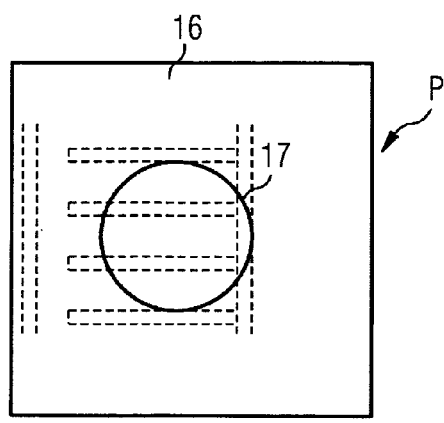
FIGS. 3 and 4 is in each case an exemplary projection.
Figure 4:
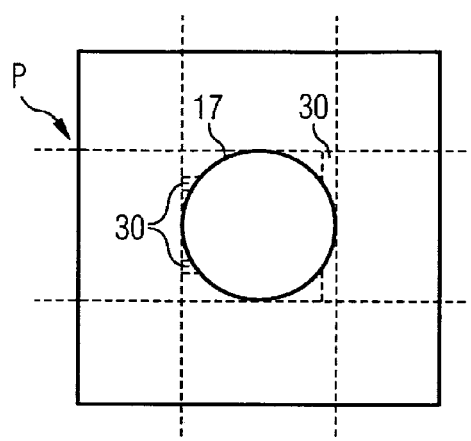

The aperture device 5 can assume different opening statuses. FIG. 3 shows by way of example a projection P that was registered with a fully open aperture device 5. FIG. 4 shows a corresponding projection P that was registered with the aperture device 5 only partially open. According to FIG. 4 the aperture device 5 has a plurality of aperture elements 20 that can be set independently of each other. According to FIGS. 3 and 4 there are only four aperture elements 20 that can only be moved left and right or, as the case may be, up and down. There can, however, be more than four aperture elements 20 and other setting options.

Figure 2:
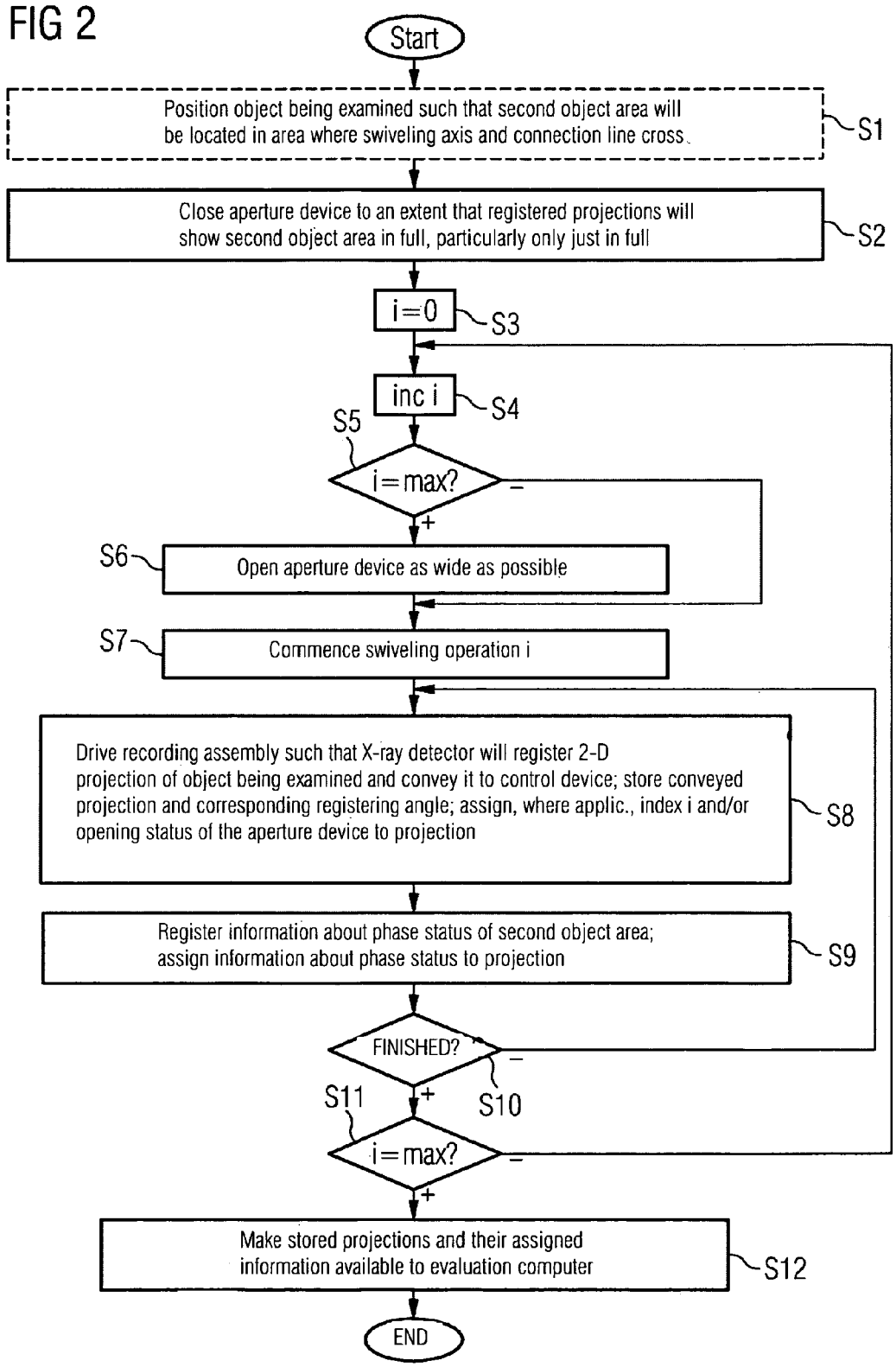
FIG. 2 is a flowchart.

Within the scope of FIG. 2 the aperture device 5 is partially closed. The aperture device 5 is, though, closed only to the extent that subsequently registered projections P of the object being examined 15 will show at least the second object area 17 in full—see FIG. 4. The aperture device 5 is therein preferably closed to the maximum possible extent. It therefore preferably remains open just wide enough for the subsequently registered projections P to show the second object area 17 only just in full—see also FIG. 4.

Step S2 could in principle be performed—like step S1 also—directly by the operator 12. What though, is preferable is for step S2 to be performed in keeping with entries made by the operator 12 but actually by the control device 1.

In the next step, S3, the control device 1 sets an index i to a start value of zero and increments the index i in a step S4. In a step S5 the control device 1 checks whether the index i has attained its maximum value max yet. If so, the control device 1 will, in a step S6, drive the aperture device 5 in such a way that it will be opened fully, which is to say as wide as possible. Operations will otherwise continue in a step S7.

In step S7 the control device 1 commences a swiveling operation. That means it starts swiveling the recording assembly 2. Said swiveling operation is continued while the ensuing steps S8 to S10 are carried out.

In step S8 the control device 1 drives the recording assembly 2 in such a way that the X-ray detector 4 registers a two-dimensional projection P of the object being examined 15 and conveys the registered projection P to the control device 1. As part of step S8 the control device 1 furthermore stores the projection P conveyed to it as well as an associated angular position $\alpha$ at which said projection P was registered.

Where applicable, it is possible for the registered projection P is be assigned not only the angular position $\alpha$ but further information, also. Possible candidates for this are, in particular, the index i and an open status B of the aperture device 5. Said information i, B is likewise assigned, where applicable, within the scope of step S8.

The assignment of tile index i, which is to say of information characteristic of the swiveling operation as such, will be especially expedient when the second object area 17 changes relatively slowly. That is because the projections P registered during a specific swiveling operation can then be used as the basis for a subsequent three-dimensional reconstruction of the object being examined 15. Assigning the opening status B is expedient especially because the expediently usable image area—see FIG. 4—of the respective projection P will then also be known immediately and without further ado.

In the present case the second object area 17 can, though, also be the heart of a person 15. The heart of the person 15 is naturally beating, meaning it is performing an iterative movement (or, in more general terms: an iterative change). Information $\phi$ about a phase condition of the second object area 17 is in this case registered—for example by means of an ECG—in a step S9 and in each case assigned to the registered projections P.

In a step S10 the control device 1 checks whether the respective swiveling operation has finished yet. If it has not, the control device 1 will return to step S8. What is achieved thereby is that the X-ray detector 4 will register a projection P in each of a multiplicity of angular positions $\alpha$ during the respective swiveling operation and convey it to the control device 1.

If, though, the swiveling operation has finished, the control device 1 will check in a step S11 whether the index i has attained its maximum value max yet. If not, the control device 1 will return to step S4. What is thus achieved thereby is that the recording assembly 2 will perform a plurality of swiveling operations.

If, though, the index i has attained its maximum value max, the control device 1 will continue the method shown in FIG. 2 in a step S12. In step S12 the control device 1 makes the stored projections P and the information α, i, B, φ assigned to the projections P available to an evaluation computer 21—see FIG. 8.

The evaluation computer 21 is as a rule a computer 21 that is different from the control device 1. In that case, conveying will take place to the evaluation computer 21. The evaluation computer 21 could, though, in individual cases also be identical to the control device 1. In that case step S12 can be dispensed with, of course.

It is further mentioned for the sake of completeness that step S12 could also be performed between steps S10 and S11 or between steps S9 and S10. In the former case, all projections P of a swiveling operation would then in each case be made available, and in the latter case in each case a single projection P.

The swiveling operations are performed over angle ranges that at least overlap. According to FIGS. 5 and 6 the angle ranges are even mutually identical because they extend from a first to a second final angular position αmin, αmax.

Figure 5:
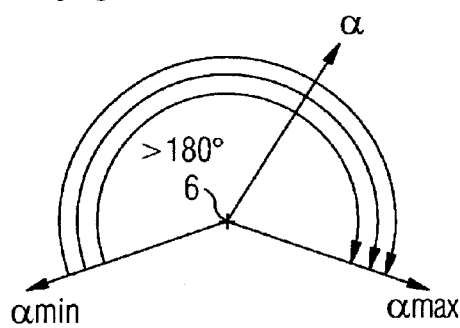
FIGS. 5 and 6 are swiveling operations.
Figure 6:
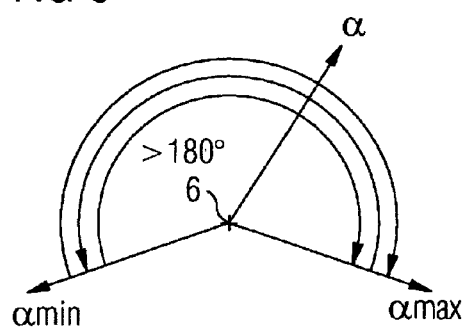

As can be seen from FIG. 5, it is possible for each swiveling operation to start at the same final angular position αmin and, accordingly, also to finish at the same final angular position αmax. In contrast to this, it can be seen from FIG. 6 that it is also possible to perform the swiveling operations alternately in the clockwise direction and in the anti-clockwise direction.

What is achieved through the procedure shown in FIG. 2—in particular through steps S5 and S6—is that the ate device 5 will be open wider during one of the swiveling operations, namely during the last swiveling operation in time, than during the other swiveling operations. Said procedure is especially advantageous because critical closing of the aperture device 5 can be performed in advance, which is to say not under time pressure. Any other swiveling operation, particularly the first swiveling operation in time, could, though, in principle also be used for this purpose. This is briefly explained below in conjunction with FIG. 7.

FIG. 7 is a variance of FIG. 2. The only difference between FIG. 7 and FIG. 2 is that steps S2 and S6 in FIG. 7 are changed over compared to those in FIG. 2 and that in step S5 the index i is checked for another value. The sequence of steps for FIG. 2 can otherwise be retained.

As mentioned already, in step S12 in FIG. 2 the projections P are made available to the evaluation computer 21 for the purpose of evaluation. According to FIG. 8, the evaluation computer 21 has a corresponding interface 22 for accepting the projections P and the information α, i, B, φ assigned to the projections P. It stores the projections P and information α, i, B. φ assigned to the projections P in a bulk storage 23.

The evaluation computer 21 has a processor unit 24 that executes a computer program 25. The computer program 25 thus determines the operating mode of the evaluation computer 21. The computer program 25 has likewise been stored in the bulk storage 23 of the evaluation computer 21. Said program can be invoked on the basis of a relevant entry made by the operator 12 so that implementing of the corresponding operating method is triggered thereby. The operator 12 makes the relevant entry via a customary input device 26, for example a keyboard/mouse combination.

Just as in the case of the control device 1, the computer program 25 must, of course, also be stored for the evaluation computer 21 in the bulk storage 23 of the evaluation computer 21. For this purpose, a corresponding data carrier 27, on which the computer program 25 is stored, can, for example, be connected in data engineering terms to the evaluation computer 21 via a corresponding interface 28 of the evaluation computer 21. The evaluation computer 21 is in that case able to transfer the computer program 25 from the data carrier 27 and store it in the bulk storage 23.

The operating mode of the evaluation computer 21 will now be explained in more detail in conjunction with FIG. 9.

As mentioned already, the evaluation computer 21 initially accepts a number of two-dimensional projections P of the object being examined 15 as well as the information α, i, B, φ assigned to the projections P. That takes place in a step S21. The projections P being the projections P dealt with in detail above, no detailed explanations will be given below concerning the projections P and the assigned information α, i, B , φ. Reference is instead made to the above elucidations relating to FIGS. 1 to 7.

In a step S22 the evaluation computer 21 accepts nominal status information Z* from the operator 12. For each projection P, in a step S23 the evaluation computer 21 then compares the status information i or, as the case may be, φ assigned to said projection P with the nominal status information Z*. If the status information i or, as the case may be, φ of the respective projection P tallies with the nominal status information Z*, then the evaluation computer 21 will determine the respective projection P relating to a basic projection P for the angular position α at which the respective projection P was registered. As has been described, therefore, the evaluation computer 21 determines a basic projection P for each of a number of angular positions α. The reference letters GP are used below for the basic projections P to distinguish the basic projections P from the other projections P.

As explained above in connection with FIG. 2, the status information i or, as the case may be, φ can, in the case of an iteratively changing second object area 17, be information about the phase condition of the second object area 17. If that is the case, the basic projections GP will in all probability stem from a plurality of swiveling operations. Different indices i will therefore have been assigned to them. Some, at least, of the basic projections GP were hence registered while the aperture device 5 was only partially open. In the procedure according to FIG. 2, for example, these are all basic projections GP where the index i does not have the maximum value max. If, on the other hand, the relevant status information is the swiveling operation as such during which the basic projections GP were registered, then it is the case either that all basic projections GP were registered with an aperture device 5 open to the maximum extent (Z*=max) or that all basic projections GP were registered with an only partially open aperture device 5 (Z*≠max). The operating method according to FIG. 9 can, though, continue being implemented regardless of which of the above-cited three cases applies.

That is because for each angular position α for which it has determined a basic projection GP the evaluation computer 21 determines an additional projection P in a step S24. To distinguish them from the basic projections GP and the projections P, the additional projections P have all been provided below with the reference letters ZP.

The additional projections ZP are independent of the status information i or, as the case may be, φ. They are determined by the fact that in their specific case the aperture device 5 was open wider than in the case of any other projection P registered at the respective angular position α.

After the additional projections ZP have been determined, using the basic projection GP and corresponding additional projection ZP, in a step S25 the evaluation computer 21 ascertains a reconstruction projection RP for the respective angular position α for each angular position α for which it has determined a basic projection GP. Using the reconstruction projections RP, in a manner known per se the evaluation computer 21 finally, in a step S26, ascertains a three-dimensional reconstruction of the object being examined 15.

Evaluations are, of course, further performed using the three-dimensional reconstruction. For example sectional representations or two-dimensional projections of the three-dimensional reconstruction can be fed out to the operator 12 via an output device 29 (in particular a display device) of the evaluation computer 21. Said evaluations are made in the manner generally customary in the state of the art. They will therefore not be dealt with in more detail below.

The basic projections GP are determined using stats information i, φ assigned directly to the projections P. The basic projections GP can therefore be determined easily and without further ado. For that reason it is not necessary to go into determining the basic projections GP in detail.

If the projections P have also been directly assigned information about the opening status B of the aperture device 5, then it will also be easily possible to ascertain the additional projections ZP, and without further ado. That is because in that case the evaluation computer 21 according to FIG. 10 can, in a step S31, fit select all projections P that were registered at a specific angular position α. Of the projections P selected in step S31, the one where the information about the opening thus B corresponds to the widest opening of the aperture device 5 is then determined in a step S32 as being the additional projection ZP.

It is, though, also possible for the evaluation computer 21 to ascertain the additional projections ZP using the projections P as such. That means it is possible for the evaluation computer 21 itself to ascertain the opening status B of the aperture device 5 for the projections P. This will be explained in more detail below in conjunction with FIG. 11.

Figure 11:
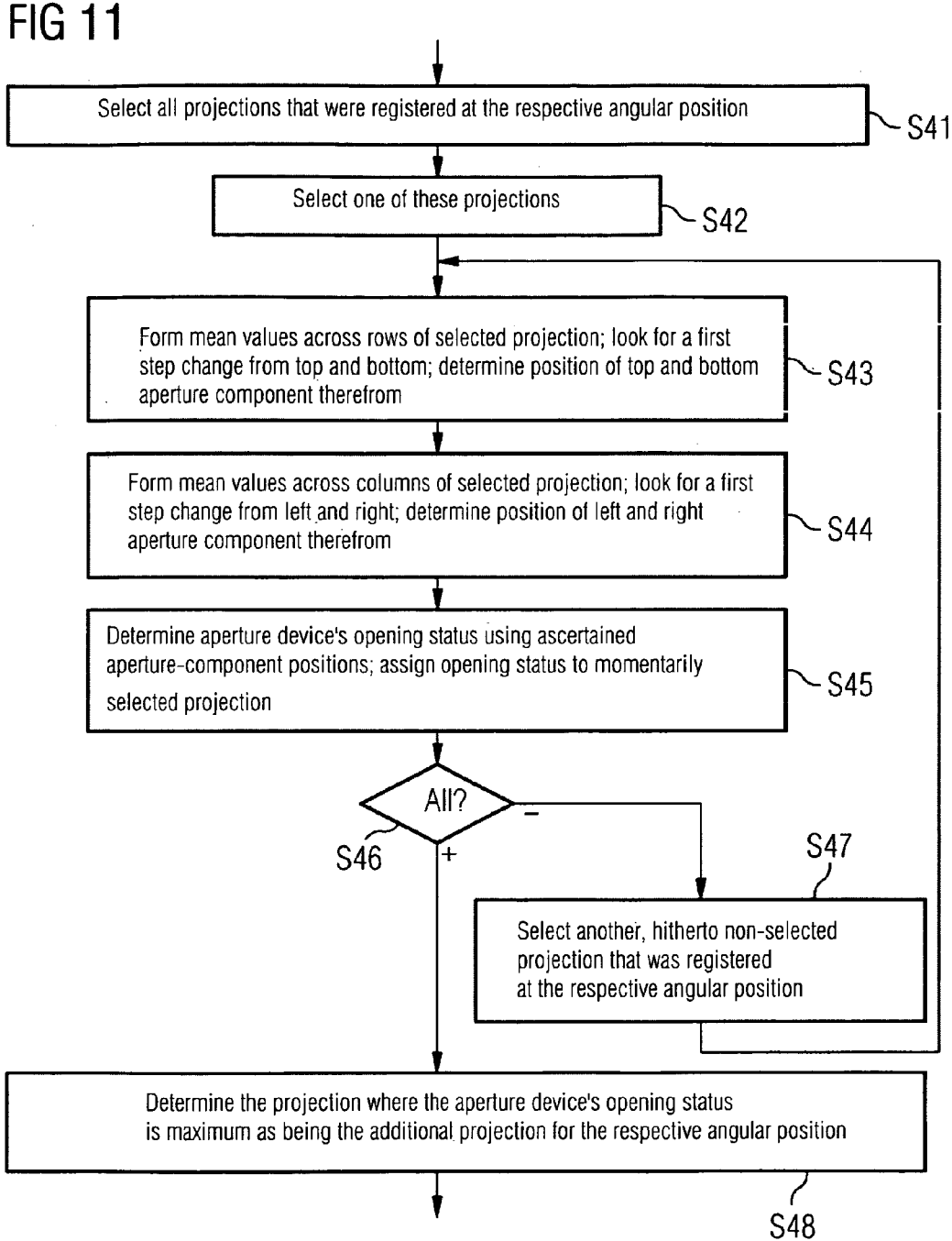

FIG. 11 has steps S41 to S48. Steps S41 and S48 here correspond to steps S31 and S32 shown in FIG. 10. Steps S41 and S48 will not, therefore, be explained, again below.

According to FIG. 11, in step S42 the evaluation computer 21 first selects one of the projections P selected in step S41. In step S43 the evaluation computer 21 then forms mean values across the rows of the selected projection P. Using the mean values it looks for a first step change from top to bottom. It determines therefrom the position of the top and bottom aperture element 20—see FIGS. 3 and 4.

In step S44 the evaluation computer 21 analogously forms the mean values across the columns of the selected projection P. It thereupon looks for the first step change from left or, as the case may be, right and determines therefrom the position of the left and right aperture element 20—see again FIGS. 3 and 4.

In a similar manner the aperture-component positions could also be determined were the situation relating to the aperture elements 20 more complex. Methods for ascertaining the aperture-component positions are, moreover, also described in DE-A-103 13 510.

Using the ascertained aperture-component positions, in step S45 the evaluation computer 21 thereupon determines the opening status B of the aperture device 5 and assigns said status to the momentarily selected projection P.

In step S46 the evaluation computer 21 checks whether it has assigned the respective opening status B to all projections P at the respective angular position α yet. If not, the evaluation computer 21 will in step S47 select another, hitherto non-selected projection P that was registered at the respective angular position α. It will thereupon return to step S43. The evaluation computer 21 will otherwise continue at step S48.

To determine the reconstruction projection RP, which is to say to implement step S25 in FIG. 9, the evaluation computer 21 preferably implements a method that will be explained in more detail below in conjunction with FIG. 12.

Figure 12:
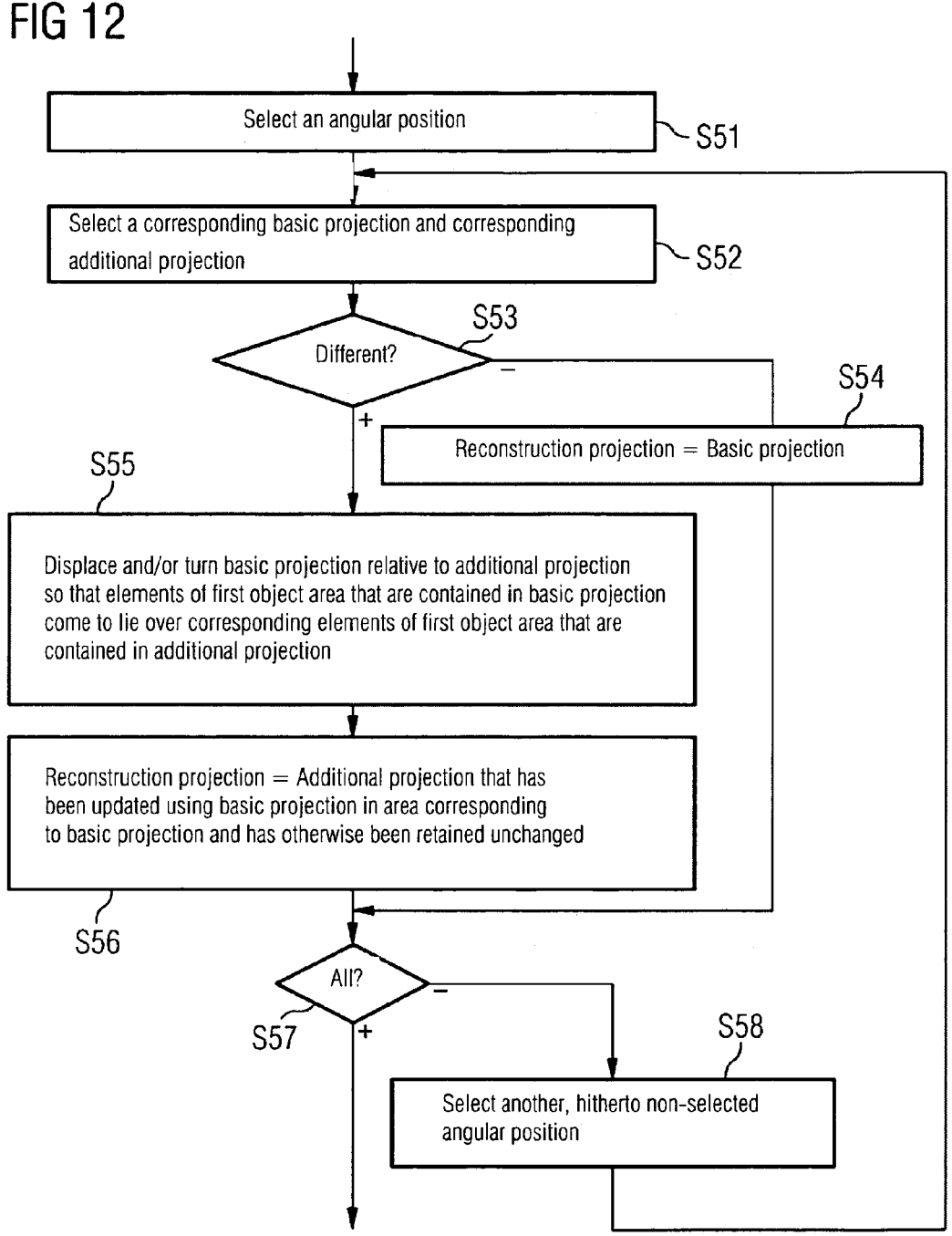

According to FIG. 12, in a step S51 the evaluation computer 21 first selects one of the angular positions α for which it has determined a basic projection GP and an additional projection ZP. In a step S52 it thereupon selects the corresponding basic projection GP and corresponding additional projection ZP for said angular position α. It is possible for the evaluation computer 21 to have determined one and the same projection P both as the basic projection GP and as the additional projection ZP. In a step S53 the evaluation computer 21 therefore checks whether the basic projection GP and additional projection ZP are projections P that are different from each other. If they are not, which is to say if the two projections GP, ZP are identical, the evaluation computer 21 will in a step S54 determine the basic projection GP as being the reconstruction projection RP for the respective angular position α. If, on the other hand, the basic projection GP and additional projection ZP are projections P that are different from each other, the evaluation computer 21 will perform steps S55 and S56.

In step S55 the evaluation computer 21 registers the basic projection GP with reference to the additional projection ZP. This is possible because, despite the fact that the aperture device 5 is open as little as possible for the basic projection GP, the basic projection GP—see FIG. 4—nonetheless contains elements 30 that were caused by the first object area 16. In step S55 the evaluation computer 21 therefore displaces and/or turns the basic projection GP relative to the additional projection ZP so that the elements 30 of the first object area 16 that are contained in the basic projection GP come to lie over corresponding elements 30 of the first object area 16 that are contained in the additional projection ZP.

The evaluation computer 21 thereupon ascertains the respective reconstruction projection RP. The reconstruction projection RP results in particular from using the additional projection ZP, with the additional projection ZP being, however, updated using the basic projection GP in an area corresponding to the basic projection GP. The additional projection ZP is otherwise retained unchanged.

In step S57 the evaluation computer 21 checks whether it has performed steps S52 to S56 for all angular positions α for which it has determined a basic projection GP yet. If not, the evaluation computer 21 will proceed to a step S58 in which it selects another, hitherto non-selected angular position α. It thereupon returns to step S52. Determining of the reconstruction projections RP has otherwise finished.

Figure 13:
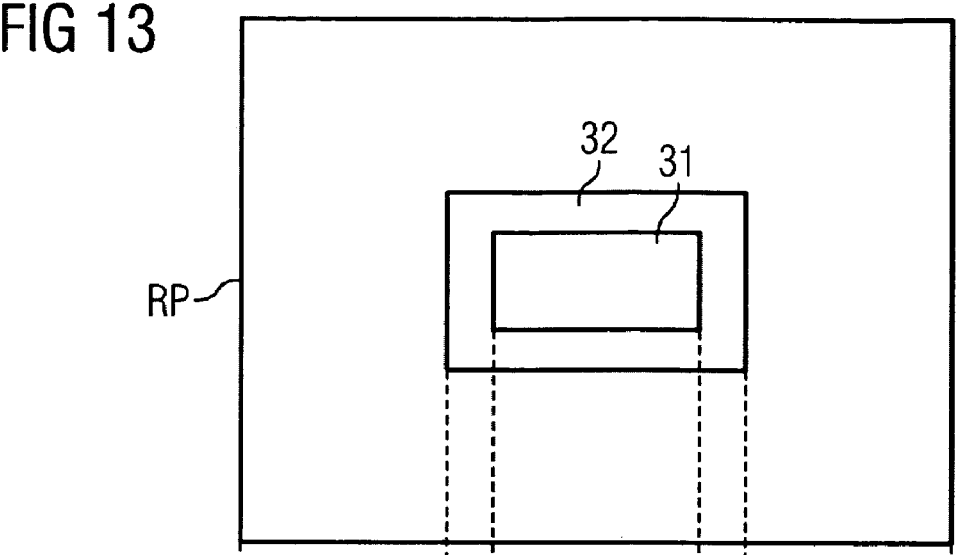
FIG. 13 is a reconstruction projection, and
FIG. 14 are weighting curves.

According to FIG. 13, the area, corresponding to the basic projection GP, of the additional projection ZP has a core 31 and an edge area 32. The edge area 32 surrounds the core 31. To implement step S56 in FIG. 12, the evaluation computer 21 always replaces the additional projection ZP in the core 31 with the basic projection GP. By contrast, different procedures are possible regarding the edge area 32.

Figure 14:
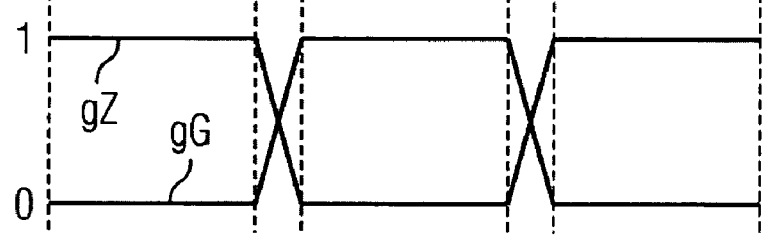

In the simplest case the evaluation computer 21 performs only simple replacing of the additional projection ZP by the corresponding area of the basic projection GP in the edge area 32, also. It is, though, also possible for the evaluation computer 21 to take account both of the basic projection GP and of the additional projection ZP for determining the reconstruction projection RP in the edge area 32. For example, the evaluation computer 21 can locally merge the basic projection GP and the additional projection ZP in the edge area 32. That is indicated in FIG. 14 for a row of the construction projection RP by, by way of example, corresponding weighting curves gG for the basic projections GP and gZ for the additional projection ZP. The evaluation computer 21 could alternatively also perform simple, non-weighted mean-value forming in the edge area 32.

As has been shown, applying the inventive procedure makes it possible to ascertain for all possible status information i, φ a three-dimensional reconstruction in which no truncation artifacts occur. The X-ray exposure of the object being examined 15 can nonetheless be kept low.

The invention claimed is:

1. An operating method for a medical X-ray apparatus having a recording assembly and a control device, comprising:
   arranging an X-ray source and an X-ray detector in the recording assembly diametrically opposite one another with reference to a swiveling axis;
   arranging an aperture device in the recording assembly between the X-ray source and the swiveling axis along a connecting line from the X-ray source to the X-ray detector;
   positioning an object having an object area constant over time and an object area changing over time in the recording assembly with the object area changing over time located in a vicinity of a crossover area of the swiveling axis and the connecting line;
   driving the recording assembly for performing a plurality of swiveling operations with at least an overlap angle range by the control device;
   registering two-dimensional projections of the object in a plurality of angular positions by the X-ray detector;
   conveying the two-dimensional projections to the control device;
   storing the conveyed two-dimensional projections along with the corresponding angular positions and status information in the control device;
   increasing an opening area of the aperture device to a maximum opening diameter of the aperture device during one of the plurality of swiveling operations; and
   in a remainder of the swiveling operations, closing the aperture device to a second opening diameter that is less than the maximum opening diameter, wherein the closing is effective to show the object area changing over time just in full.

2. The operating method as claimed in claim 1, wherein the control device stores an opening status of the aperture device.

3. The operating method as claimed in claim 1, wherein the object area changing over time changes iteratively.

4. The operating method as claimed in claim 1, wherein the status information comprises a phase condition of the object area changing over time assigned to a respective projection and a characteristic of a swiveling operation during which the respective projection is registered.

5. The operating method as claimed in claim 1, wherein a computer program is stored in the control device for operating the recording assembly.

6. The operating method as claimed in claim 1, wherein the connecting line is an X-ray beam from the X-ray source to the X-ray detector.

7. The operating method as claimed in claim 1, wherein:
   the object is a human patient,
   the object area constant over time is a skeletal area of the human patient, and
   the object area changing over time is a heart of the human patient.

8. A medical X-ray apparatus, comprising:
   a recording assembly that records a plurality of two-dimensional projections of an object that comprises an object area constant over time and an object area changing over time in a plurality of angular positions;
   an X-ray source and an X-ray detector in the recording assembly that are arranged diametrically opposite one another with reference to a swiveling axis;
   an aperture device in the recording assembly that is arranged between the X-ray source and the swiveling axis along a connecting line from the X-ray source to the X-ray detector;
   a control device that operates the recording assembly via an interface;
   a storage unit in the control device that stores the operating computer program and the projections of the object along with a corresponding angular position and status information about the object area changing over time and a characteristic of a swiveling operation;
   a processor unit in the control device that executes the operating computer program; and
   an I/O interface in the control device that triggers the execution by an operator; and
   an evaluation device for determining a basic projection for each of the plurality of angular positions in the plurality of two-dimensional projections and for determining an additional projection for each basic projection having a wider opening area of the aperture device than a projection of the remaining two-dimensional projections at each of the plurality of angular positions.

9. An operating method for a computer in a medical X-ray apparatus, comprising:
   connecting the computer to an X-ray recording assembly, the X-ray recording assembly comprising:
   an X-ray source and an X-ray detector in the recording assembly diametrically opposite one another with reference to a swiveling axis, and
   an aperture device in the recording assembly between the X-ray source and the swiveling axis along a connecting line from the X-ray source to the X-ray detector;
   positioning an object having an object area constant over time and an object area changing over time in the recording assembly with the object area changing over time located in a vicinity of a crossover area of the swiveling axis and the connecting line;
   registering a plurality of two-dimensional projections of the object in a plurality of angular positions by the X-ray detector;
   conveying the two-dimensional projections of the object to the computer;
   determining a basic projection for each of the angular positions in the two-dimensional projections with a status information about the object area changing over time corresponding to a nominal status information about the object area changing over time;
   determining an additional projection for the basic projection having a wider opening area of the aperture device than a projection of the remaining two-dimensional projections at the respective angular position;
   reconstructing a projection based on the basic projection and the respectively corresponding additional projection for each respective angular position; and
   ascertaining a three-dimensional reconstruction of the object based on projection.

10. The operating method as claimed in claim 9, wherein the object area changing over time changes iteratively.

11. The operating method as claimed in claim 9, wherein the status information comprises a phase condition of the object area changing over time assigned to a respective projection and a characteristic of a swiveling operation during which the respective projection is registered.

12. The operating method as claimed in claim 9, wherein an opening status of the aperture device is assigned to each of the projections.

13. The operating method as claimed in claim 9, wherein the reconstruction projection is reconstructed by updating the additional projection in an area corresponding to the basic projection which is different to the basic projection.

14. The operating method as claimed in claim 13, wherein the area of the additional projection corresponding to the basic projection is replaced by the basic projection.

15. The operating method as claimed in claim 13, wherein the area of the additional projection corresponding to the basic projection comprises a core and an edge area surrounding the core.

16. The operating method as claimed in claim 15, wherein the core of the additional projection is replaced with the basic projection and the edge area is locally merged with the basic projection.

17. The operating method as claimed in claim 13, wherein the basic projection comprises an element of the object area constant over time and the basic projection is registered to the additional projection based on the element.

18. The operating method as claimed in claim 9, wherein a computer program is stored in the computer for implementing the operating method.

19. The operating method as claimed in claim 9, wherein:
   the object is a human patient,
   the object area constant over time is a skeletal area of the human patient, and
   the object area changing over time is a heart of the human patient.

20. The operating method as claimed in claim 1, wherein the increasing an opening area of the aperture device to a maximum opening diameter of the aperture device is done in a last one of the plurality of swiveling operations.

21. The operating method as claimed in claim 1, wherein the increasing an opening area of the aperture device to a maximum opening diameter of the aperture device is done in a first one of the plurality of swiveling operations.

* * * * *